(12) United States Patent
Jiang et al.

(10) Patent No.: US 10,092,616 B2
(45) Date of Patent: Oct. 9, 2018

(54) COMPOSITION OF CHINESE MEDICINES AND APPLICATION METHOD THEREOF FOR EXTERNALLY TREATMENT FOR HYPERTENSION

(71) Applicants: Tianfeng Jiang, Alhambra, CA (US); Zhenghua Jiang, Alhambra, CA (US); Jinrong Zhou, Alhambra, CA (US)

(72) Inventors: Tianfeng Jiang, Alhambra, CA (US); Zhenghua Jiang, Alhambra, CA (US); Jinrong Zhou, Alhambra, CA (US)

( * ) Notice: Subject to any disclaimer, the term of this patent is extended or adjusted under 35 U.S.C. 154(b) by 35 days.

(21) Appl. No.: 15/381,068

(22) Filed: Dec. 15, 2016

(65) Prior Publication Data

US 2017/0368129 A1 Dec. 28, 2017

(51) Int. Cl.

| | | |
|---|---|---|
| *A61K 36/00* | (2006.01) |
| *A61K 36/888* | (2006.01) |
| *A61K 36/754* | (2006.01) |
| *A61K 36/236* | (2006.01) |
| *A61K 36/28* | (2006.01) |
| *A61K 36/232* | (2006.01) |
| *A61K 36/536* | (2006.01) |
| *A61K 36/185* | (2006.01) |
| *A61K 36/481* | (2006.01) |
| *A61K 36/74* | (2006.01) |
| *A61K 36/268* | (2006.01) |

(52) U.S. Cl.
CPC .......... *A61K 36/888* (2013.01); *A61K 36/185* (2013.01); *A61K 36/232* (2013.01); *A61K 36/236* (2013.01); *A61K 36/268* (2013.01); *A61K 36/28* (2013.01); *A61K 36/481* (2013.01); *A61K 36/536* (2013.01); *A61K 36/74* (2013.01); *A61K 36/754* (2013.01)

(58) Field of Classification Search
CPC ...................................................... A61K 36/00
See application file for complete search history.

*Primary Examiner* — Qiuwen Mi
(74) *Attorney, Agent, or Firm* — WPAT, P.C., Intellectual Property Attorneys; Anthony King

(57) ABSTRACT

A composition of Chinese medicines for externally treatment for hypertension includes following herbs: evodia rutaecarpa, chuanxiong, sunflower disc, rhizoma typhonii, *angelica, prunella vulgaris, taxillus chinenesis*, herba siegesbeckiae, *chamomile, astragalus, uncaria rhynchophylla, asarum*, and *burdock*, wherein a weight ratio of the composition is: evodia rutaecarpa 40-50, chuanxiong 30-40, sunflower disc 20-30, rhizoma typhonii 20-25, angelica 20-25, prunella vulgaris 20-30, herba siegesbeckiae 20-30, *taxillus chinenesis* 20-30, *chamomile* 20-25, astragalus 20-25, uncaria rhynchophylla 20-30, asarum 20-25, and burdock 20-25.

15 Claims, No Drawings

COMPOSITION OF CHINESE MEDICINES AND APPLICATION METHOD THEREOF FOR EXTERNALLY TREATMENT FOR HYPERTENSION

CROSS REFERENCE OF RELATED APPLICATION

This is a non-provisional application that claims priority under 35 U.S.C. 119(a-d) to Chinese application number 201610454154.7, filed Jun. 27, 2016. The afore-mentioned patent applications are hereby incorporated by reference in their entireties.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to Chinese medicines, and more particularly to a composition of Chinese medicines and application method thereof for externally treatment for hypertension.

Description of Related Arts

Chinese medicine practitioners consider that human foot and visceral organs have close relationship with each other. Every organ of a human body has a corresponding reflex zone distributed on the feet of a person. The foot reflex zones can be cataloged into two concepts. Firstly, the sole of a foot is correspondingly related to the visceral organs; the instep of a foot is correspondingly related to the body; the inside surface of a foot is correspondingly related to the ridge; the outside surface of a foot is correspondingly related to limbs; the heel of a foot is correspondingly related to pelvic cavity. Secondly, the concept of "up side down corresponding", "head crossing", and "same left and same right". The soles are correspondingly related to visceral organs, wherein the reflex zones of the soles of the feet are corresponding to the visceral organs such as heart, liver, spleen, lung, and kidney. The insteps are correspondingly related to the human body and face, wherein the reflex zones of the insteps of the feet are corresponding to the human body portion and face portion, such as the ribs and the face. The inside surfaces are correspondingly related to the mid-spine, wherein the reflex zones of the inside surfaces of the feet are corresponding to the human spine and organs, such as nose and bladder, distributed along a midline of the spine. The heels are correspondingly related to the pelvic cavity, wherein the reflex zones of the heels of the feet are corresponding to pelvis cavity portion of the human body, such as testicle, ovary, urethra, vaginal, uterus, prostate, buttock, and etc.

The concept of "up and down corresponding" represents the fact that the reflex zones distributed along the toes to the heels are corresponding to the organs from the head to the buttock of the person. The concept of "head crossing" represents that organs of the head of a person have corresponding reflex zones distributed on the toes, wherein since the human nerves are extended downwardly in a crossing manner from the neck portion, the organs of the left head are corresponding to the right foot and the organs of the right head are corresponding to the left foot. For example, the reflex zone of the left eye is correspondingly provided at the right foot. The concept of "same left and same right" represents that the reflex zones of the organs of the left body (such as heart, spleen, descending colon, and sigmoid colon) are correspondingly provided at the left foot, and the reflex zones of the organs of the right body (such as liver, gallbladder, cecum, appendix, and ascending colon) are correspondingly provided at the right foot. In addition, symmetric organs of the human body (lung, kidney, and ureter) also have reflex zones of the feet that also follows the concept of "same left and same right".

Feet are important parts of the human body, which are located in the lowest positions of the human body, wherein each foot is made up 26 bones, 33 joints, 20 muscles, and more than 100 ligaments. All the organs of the human body have corresponding reflex zones provided at the soles of the feet. Only one side of the foot has six meridians (main and collateral channels) passing through and more than 30 acupoints, so foot is one of human portions which has the most intensive region of meridians and acupoints. Also, foot perfectly supports the full weight of the human body and has close relationship with the human physical health.

With the improvement of the quality of life, there are more and more people focused on healthcare. People soak their feet into hot water every day, which can promote blood circulation and eliminate fatigue. There are more and more people soak their feet in health-oriented Chinese medicine bath, which uses the hot water to promote Chinese medicine penetration into their human body, so as to ensure the Chinese medicine penetrating through the feet to the body's meridians that would not cause oral overdose which is leading to adverse reactions.

At present, more and more patients have hypertension, and the disease incidence of hypertension continually show an upward trend. The hypertension has high disease incidence, high disability rate, and high mortality. And, the awareness rate cure rate, and control of treatment rate of hypertension are as low as 50%, 40% and 10% respectively. Research has shown that long term blood pressure more than 135/85 mmHg will cause damage to the human body. A diagnostic criterion for high blood pressure is 140/90 mmHg while the ideal blood pressure is 120/80 mmHg. Form a clinical point of view, high blood pressure will mainly cause vascular injury. It is found that short term high blood pressure will also cause acute injuries and gradually increasing of blood pressure for long term will cause chronic injuries too. In general, the hypertension has extensive damage to multiple organs of human body that it is one of the main causes of disabilities sudden death. Since the damage to the human body due to high blood pressure is unconsciously and slowly developing, the high blood pressure is often easy to be ignored by people. Therefore, when damages due to the high blood pressure are discovered, it is usually severe and irreversible that it is hard to cure and recover even after treated with a lot of medicines, so that the hypertension is called as a silent killer. Therefore, the hypertension is required to be prevented and be treated in the early state. The hypertension can be controlled by drug therapies with daily life adjustments to avoid deterioration of condition. It is also well known that the damage of the hypertension is a long and slow process, and once people have hypertensions, they need to take lifelong medicine while it is still hard to cure completely. In addition, the hypertension medicine has strong side effects to the human body.

SUMMARY OF THE PRESENT INVENTION

The invention is advantageous in that it provides a composition of Chinese medicines for externally treating the hypertension which is able to overcome the shortcomings of existing technology.

Another advantage of the invention is to provide an application method of the composition of Chinese medicines for externally treatment for hypertension.

Another advantage of the invention is to provide a solution for solving existing hypertensive disease which needs lifelong medication problems and having side effects on the human body.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

A composition of Chinese medicine for externally treatment for hypertension according to a preferred embodiment of the present invention comprises the following herbs: evodia rutaecarpa (吳茱萸), chuanxiong (川芎), sunflower disc (葵花盘), rhizoma typhonii (白附子), *angelica* (白芷), *prunella vulgaris* (夏枯草), *taxillus chinensis* (豨莶草), herba siegesbeckiae (桑寄生), *chamomile* (菊花), *astragalus* (黄芪), *uncaria rhynchophylla* (钩藤), *asarum* (细辛) and *burdock* (牛蒡).

The weight ratio of the composition is: evodia rutaecarpa 40-50:chuanxiong 30-40, sunflower disc 20-30:rhizoma typhonii 20-25:*angelica* 20-25:*prunella vulgaris* 20-30: herba siegesbeckiae 20-30:*taxillus chinenesis* 20-30:*chamomile* 20-25:*astragalus* 20-25:*uncaria rhynchophylla* 20-30: *asarum* 20-25:*burdock* 20-25. For example, if the weight unit is grams, then the composition comprises 40 g-50 g of evodia rutaecarpa, 30 g-40 g of chuanxiong, 20 g-30 g of sunflower disc, 20 g-25 g of rhizoma typhonii, 20 g-25 g of *angelica*, 20 g-30 g of *prunella vulgaris*, 20 g-30 g of herba siegesbeckiae, 20 g-30 g of *taxillus chinenesis*, 20 g-25 g of *chamomile,* 20 g-25 g of *astragalus*, 20 g-30 g of *uncaria rhynchophylla,* 20 g-25 g of *asarum*, and 20 g-25 g of *burdock.*

Preferably, a first alternative mode of the weight ratio of the composition of Chinese medicine for externally treatment for hypertension is: evodia rutaecarpa 35-40, chuanxiong 25-30, sunflower disc 22-28, rhizoma typhonii 21-24, *angelica* 21-24, *prunella vulgaris* 22-28, herba siegesbeckiae 22-28, *taxillus chinenesis* 22-28, *chamomile* 21-24, *astragalus* 21-24, *uncaria rhynchophylla* 21-38, *asarum* 21-24, and *burdock* 21-24. Also, if the weight unit of the composition, for example, is grams, then the composition comprises 35 g-40 g of evodia rutaecarpa, 25 g-30 g of chuanxiong, 22 g-28 g of sunflower disc, 21 g-24 g of rhizoma typhonii, 21 g-24 g of *angelica*, 22 g-28 g of *prunella vulgaris,* 22 g-28 g of herba siegesbeckiae, 22 g-28 g of *taxillus chinenesis*, 21 g-24 g of *chamomile*, 21 g-24 g of *astragalus*, 21 g-38 g of *uncaria rhynchophylla*, 21 g-24 g of *asarum*, and 21 g-24 g of *burdock.*

Preferably, a second alternative mode of the weight ratio of the composition of Chinese medicine for externally treatment for hypertension is: evodia rutaecarpa 38, chuanxiong 28, sunflower disc 25, rhizoma typhonii 22, *angelica* 22, *prunella vulgaris* 25, herba siegesbeckiae 25, *taxillus chinenesis* 25, *chamomile* 25, *astragalus* 22, *uncaria rhynchophylla* 25, *asarum* 22, and *burdock* 22. Also, if the weight unit of the composition, for example, is grams, then the composition comprises 38 g of evodia rutaecarpa, 28 g of chuanxiong, 25 g of sunflower disc, 22 g of rhizoma typhonii, 22 g of *angelica*, 25 g of *prunella vulgaris*, 25 g of herba siegesbeckiae, 25 g of *taxillus chinenesis*, 25 g of *chamomile,* 22 g of *astragalus*, 25 g of *uncaria rhynchophylla,* 22 g of *asarum*, and 22 g of *burdock.*

Accordingly, the composition of Chinese medicines for externally treatment for hypertension is in powder or decoction form.

The composition of Chinese medicines according to the above embodiments of the present invention is adapted for external treatment for a hypertension patient by feet soaking or bathing, wherein an application method of the composition of Chinese medicine comprises the following steps:

(a) Add a predetermined amount of the composition in powder or decoction form into a basin for feet soaking or bathing.

(b) Brew the powder or decoction composition with hot water having a temperature more than 40° C., preferably 40° C.~100° C. and well mix to form a composition solution. The proportion of the composition and hot water is 30~50: 2000~4000. Accordingly, if 30~50 grams or ml of the composition is used, it is brewed and mixed with 2000~4000 ml of hot water.

(c) Apply steam of the composition solution made by brewing and mixing the power or decoction composition with 2000 ml hot water with a temperature 40° C.~100° C., preferably 70° C.~80° C., for fumigating the feet of the user for about 10 minutes.

(d) Wait until the composition solution being cool to 38° C.~48° C., preferably 40° C.~42° C., and, preferably add another 2000 ml of water with a temperature of 38° C.~48° C., preferably 40° C.~42° C.

(e) Soak the feet of the user in the composition solution, preferably maintaining at 40° C.~42° C., for 20~40 minutes, preferably 30 minutes.

(f) Reply the steps (a) to (e) at least once per day at a time after dark and before dawn, preferably 30 minutes before sleeping.

By means of the feet soaking or bathing application method of the composition of Chinese medicines according to the above preferred embodiment of the present invention, the sunflower disc and evodia rutaecarpa are for lowering blood pressure; the *prunella vulgaris, chamomile, uncaria rhynchophylla*, and herba siegesbeckiae are for blood pressure auxiliary lowering blood pressure; the chuanxiong,

*angelica*, rhizoma typhonii, and *asarum* are for promoting blood and Qi circulation; the *astragalus, taxillus chinenesis* and *burdock* are for strengthen immunity and metabolism. Therefore, the minimum effective elements of the composition for external treatment, i.e. feet soaking or bathing, for hypertension include the evodia rutaecarpa, sunflower disc, chuanxiong, and *astragalus*. The *prunella vulgaris*, the *chamomile*, the herba siegesbeckiae, the *angelica*, the rhizoma typhonii, the *asarum*, the *taxillus chinenesis*, and the *burdock* are optional auxiliary element to be selected to enhance the blood pressure lowering effects.

The effects of the composition of the Chinese medicines for externally treatment for hypertension are illustrated as follows:

Evodia rutaecarpa: nature in bitter and hot; good for liver, spleen, stomach, and kidney; having ability for suspending thermal and reducing pain, and preventing vomiting; having ability to cure pain, cold stomach, vomiting, diarrhea, mouth sore, throat ache, and eczema. Based on the modern research, evodia rutaecarpa has strong pharmacological effects on gastrointestinal system, intestinal system, cardiovascular system, bronchial contraction, analgesic, anti-inflammatory, anti-oxidation, weight loss, and anus sphincter relaxation; In clinic, the evodia rutaecarpa is adapted to cure chronic atrophy gastritis, stomach spasm, ulcer and colon inflammatory, drooling of children, oral ulcers of infants, menstrual pain, hypertension, mumps of children, and heel pains.

Chuanxiong: nature in hot and warm; good for liver, gallbladder, and heart; having ability to promote blood circulation, removing wind pain, and alleviate mental depress; being able to cure abdominal pain, chest discomfort, heartache, felling injury pain, sores, and swelling pain, menstrual pain, postpartum pain, headache, toothache, rheumatism pain and eye swelling pain. Based on the modern research, chuanxiong has strong pharmacological effects on cardiovascular system, crown pulse flow, brain cycle, blood microcirculation, outside vascular, blood pressure, blood system, smooth muscle, urinary system, respiratory, central nervous system, and the anti-radiation. In clinic, the chuanxiong is adapted to cure coronary heart disease, cerebral ischemia disease, craniocerebral trauma, migraines, severe pulmonary heart disease, bronchial asthma, severe hepatitis, chronic nephritis, and hypertension during pregnancy.

Sunflower disc: sweet flavor and cold in nature; good for remove heat, pain, bleeding and smooth liver; having ability to cure high blood pressure, headaches, dizziness, tinnitus, epigastric pain, dysmenorrhea, uterine bleeding, and sore rashes.

Rhizoma typhonii: nature in hot, warm, and toxic; good for stomach and liver; having ability to remove wind phlegm, detoxification, and remove pain; having ability to cure stroke, phlegm backwater, oblique mouth and eyes, tetanus, vertigo, headache, swelling pain, viper bite injury, and tuberculosis. In modern research, the *angelica* is able to calm down the mood, cure convulsions, prevent bacteria, and improve immune, and cure cancer. In clinic, the *angelica* is able to cure epilepsy, surface neural paralysis, trigeminal nerve pain, neck lymph nodes nuclear, migraines, and vitiligo, chloasma, spotted tinea, sweat stain and brain vascular disease.

*Angelica*: nature in hot and warm; good for lung, stomach, and intestine; being able to remove wind, remove wind pain, remove swelling pain, prevent vomiting, cure postpartum abdominal pain, cure metrorrhagia, cure metrostaxis, cure hemorrhoids blood, cure skin itching, cure freckles acne, cure spleen and stomach discord, and cure intestinal dirty. In the modern research, the *angelica* has strong pharmacological effects on antibacterial, analgesic, anti-inflammatory, anti-oxidation, and photosensitive. In clinic, the *angelica* is used to cure headaches, stomach pain, rhinitis, sinusitis, traumatic ulcer, eczema, eczema, scald, hordeolum, mastitis, acne, and chloasma.

*Prunella vulgaris*: nature in bitter, hot, cold, and nontoxic; good for liver and gallbladder; bingable to clear liver and eyesight, cool blood bleeding, release swelling, release cough, release heat, and has detoxification effect. The *prunella vularis* has strong pharmacological effects on lymph nodes nuclear, goiter, vertigo, tuberculosis, oblique mouth and eyes, bone pain, acute infectious jaundice type hepatitis, and the bacillary dysentery. In modern research, the *prunella vularis* also has strong effect for reducing blood pressure, anti-inflammatory, antibacterial, inhibiting immune, and drop blood sugar.

Herba siegesbeckiae: nature in bitter, hot, and cold; good for liver and kidney; being able to remove rheumatism, strong joint, and perform detoxification; having strong treatment on rheumatism, paralyzation, skin rubella, eczema for itch, sores, hot and humid jaundice and the hypertension. In modern research, the herba sirgesbeckiae has pharmacological effects on anti-inflammatory, analgesic, check itch, and immune function. In clinic, the herba siegesbeckiae has strong treatment effects on rheumatism arthritis, gout arthritis, back pain, coronary heart disease, and high blood pressure.

*Taxillus chinenesis*: nature in bitter and sweet; good for liver and kidney; having treatment effects on removing rheumatism, liver, kidney, strong bones, and good for pregnant; having treatment effects on rheumatism pain, kidney weak, waist back pain, liver and kidney weak, fetal movement, and pregnancy edema. In modern research, the *taxillus chinenesis* has strong pharmacological effects on immune, anti-inflammatory, and anti-1 type allergy reaction. In clinic, the *taxillus chinenesis* has treatment effects on arthritis, lumbar disc herniation, uremia, threatened abortion, habitual abortion, hypertension, virus myocarditis acute period, and recovery period contraction, high blood lipids.

*Chamomile*: nature in sweet, bitter, and slightly cold; having treatment effects on remove heat, clear eyes, clear lung, and detoxification; having treatment effects on wind hot cold, fever headache, headache dazzled, accounts red Dim, small in pupil, red and glare face, vertigo, tinea, phlegm, and swelling pain. In modern research, the *chamomile* has strong pharmacological effects on antibacterial, resistance HIV, antipyretic, anti-inflammatory, anti-oxidation, anti-aging, and on cardiovascular system. In clinic, the *chamomile* has treatment effects on fever, urgent, chronic pharyngitis, headache, trigeminal neuralgia, hypertension, vertigo, trachoma, rhinitis, sinusitis, and hordeolum.

*Astragalus*: sweet in flavor and nature in warm; good for lung and spleen; having treatment effects on raising blood and strong health muscles; having treatment effects on temper weak, falling organs, weak lung, short breath, cough, sweat, less urine, puffy, blood lost, blood stasis, and blood weak. In modern research, the *astragalus* has pharmacological effects on immune system, body metabolism, cardiovascular system, anti-aging, urinary system, liver, nerve and endocrine systems. In clinic, the *astragalus* has strong pharmacological effects on respiratory infection, asthma, high altitude pulmonary heart disease, viral myocarditis, heart failure, ischemic heart disease, chronic nephritis, rhinitis, myocardial infarction, viral myocarditis and cerebral thrombosis.

*Uncaria rhynchophylla*: sweet flavor and nature in slightly cold; having treatment effects on removing heat, clear liver, spasm, fever, children night crying, headache, and vertigo; having good effects on reducing blood pressure. In modern research, the *uncaria rhynchophylla* has pharmacological effects on cardiovascular system, anti-experiment rhythm disorders, central nervous system, anti-convulsions, anti-epilepsy, brain protection, nerve cells, blood system, immune function, and anticancer. In clinic, the *uncaria rhynchophylla* has strong pharmacological effects on hypertension, headache, migraines, trigeminal nerve pain, irritable syndrome, pediatric diseases and so on.

*Asarum*: nature in bitter and warm; good for heart, lung, and kidney; having treatment effect on removing wind cold, removing wind pain, tongqiao, lung, cold, headache, toothache, nasal problems, running noise, eyes pain, damaged ear, sore throat, aphtha, phlegm problems, cough, pain knee, ascariasis, abdominal pain, dysmenorrhea, chest pain, heartache, phlegm, and epilepsy fainting. In modern research, the *asarum* has strong pharmacological effects on antipyretic, analgesic, anesthesia, anti-inflammatory, respiratory, immune resistance, toothache, sciatica, rheumatoid arthritis, chronic bronchitis, chronic simple rhinitis, impotence, premature ejaculation, oral ulcers, plateau frostbite, refractory ulcer, abdominal pain, and five epsom.

*Burdock*: nature in hot, bitter, and cold; good for lung and stomach; having treatment effects on evacuation wind hot, lung, detoxification, wind hot cold, temperature disease, measles, rubella, swollen sores, scrofula phlegm, swollen cheek, throat pain, throat swelling, and cough phlegm. In modern research, the *burdock* has pharmacological effects on anti-virus, cough, reduce blood sugar, anti-nephropathy, anti-oxidation, and anti-tumor. In clinic, the *burdock* has treatment effects for facial paralysis, sinusitis, arthritis, and the diabetes nephropathy.

The composition of Chinese medicines for externally treatment for hypertension according to the preferred embodiment of the present invention is illustrated. Clinical trials are illustrated as follows:

Processing: accurate weight 38 grams of evodia rutaecarpa, 28 grams of chuanxiong, 25 grams of sunflower disc, 22 grams of rhizoma typhonii, 22 grams of *angelica*, 25 grams of *prunella vulgaris*, 25 grams of herba siegesbeckiae, 25 grams of *taxillus chinenesis*, 22 grams of *chamomile*, 22 grams of *astragalus*, 25 grams of *uncaria rhynchophylla*, 22 grams of *asarum*, and 22 grams of *burdock*, which are mill and mix to 100-160 mesh fine powder, wherein each 40 grams of such powder composition is concealed and packed in a bag made of liquid permeable material, such as spinning cloth.

Application method: (1) Add 40 grams of fine powder composition or simply put the bag containing the 40 grams of fine powder composition into a basin, and brew and mix with 2000 ml boiling water to form a composition solution. (2) Apply medicine steam of the composition solution for fumigating feet for 10 minutes. (3) Wait until the hot composition solution being cool to 40° C.~42° C., preferably adding another 2000 ml of water with a temperature of 40° C.~42° C., and soak the feet into the composition solution for 20-30 minutes. (4) Reply the steps (1) to (3) once per day before sleeping. The application method further comprises step (3.1): Measure blood pressure every 20-30 minutes when the feet are soaked into the composition solution, wherein the best time to soak the feet into the composition solution is 9 pm. A complete treatment course is preferable 30 days.

Information: Sample 50 cases, with male and female patients, age ranging between 45 to 85 years old, including 50% of patients having mild to moderate level of hypertension, and including 50% of patients having severe level of hypertension.

Observation criteria: the blood pressure of the patients having hypertension is measured after the normal blood pressure is observed.

Result: Feet bathing or soaking before sleeping once a day; after a 30 days course, the blood pressure becomes normal. After 3 courses, the blood pressure becomes stable. Then, stop taking feet bathing and the blood pressure remains normal.

The patients have feet bathing or soaking every day before sleeping according to the above mentioned preferred embodiment for 3 courses, and stop after 3 courses, the blood pressure of the patients remain normal within six months.

Summary: the sampled 50 cases include 46 effective cases, that is 92%; 35 obviously effective cases, that is 70%; 4 non-effective cases, that is 4.8%.

Typical cases of clinical trials are shown as follows:

(1) Miss/Mrs. Chen, female, 65 years old, having hypertension for the past 10 years, blood pressure: 140/90 mmHg. At first, she didn't take any medicine, and she has headache and dizziness after years, and syndrome. Then, she went to hospital and found her blood pressure is around 155/95 mm/Hg. The doctor recommended her to take medicine and cannot stop taking medicine. But, taking medicine has strong side effects on her. She took the composition of the present invention by feet bathing or soaking every day at 9 p.m. before sleeping for 20-30 minutes, and then measured her blood pressure, while at the same time, taking medicine. After one course, her blood pressure basically became normal, and her headache and dizziness had improved; She continuously applied the present invention for 3 courses, and her blood pressure became 130/85 mmHg, and her headache and dizziness symptoms disappeared. After 3 courses, she stopped taking medicines, and continuously took the composition of the present invention by feet bathing or soaking for 6 months. Her blood pressure became 125/85 mmHg. Finally, her blood pressure remains normal without taking medicine.

(2) Miss/Mrs. Lee, 48 years old, having hypertension for the past 14 years, blood pressure: 145/90 mmHg, which is a first level of hypertension. The doctor recommends her taking medicine and cannot be stopped. However, considering to her age, she decided to try a mild treatment method of the present invention. She took the composition of the present invention by feet bathing every day at 9 p.m. before sleeping for 20-30 minutes, and then measured her blood pressure, while taking medicine at the same time. After one treatment course, the blood pressure basically becomes normal, but still not stable. She continuously applied the composition of the present invention for 3 courses, and her blood pressure became 120/80 mmHg. After 3 courses, she stops taking medicines, and continuously takes the composition of the present invention by feet bathing until now, her blood pressure remains normal without taking medicine.

(3) Mr. Zhao, 80 years old, having hypertension for the past 20 years, which is a serve level of hypertension, and he takes medicine for a long time. His highest blood pressure: 200 mmHg and the normal blood pressure for him is 175/105 mmHg. He feels headache and dizziness every day, and cannot fall asleep. The doctor insists that he needs to take medicines and uses the heavier dose when the blood pressure is too high. He took the composition of the present invention by feet bathing every day at 9 p.m. before sleeping for 20-30 minutes, and then measured his blood pressure, while at the same time, taking medicine. After one course, his blood pressure reduced, but still higher than normal people. He continuously took the present invention for 3 courses, and his blood pressure became 150/95 mmHg. He continuously takes the composition of the present invention by feet bathing until now while at the same time taking medicines. His blood pressure remains normal without taking heavier dose of medicine and his headache and dizziness dramatically reduces.

The composition of Chinese medicines for external treatment for hypertension and the application method thereof Chinese have the following advantages:

1. The feet bath can make viscera recovery balance, blood system recovery in smooth blood pressure, and completely reverse hypertension cure mechanism. The present invention changes the past hypertension treatment that the patients need to take medicines for lifelong, that avoids gastrointestinal stimulus and liver kidney injury. After long-term taking the composition of Chinese medicines of the present invention by feet bathing, the brain kidney function also will unknowingly enhance. It can activate immunities, improve self-healing diseases capacities, and avoid many species heart brain vascular diseases.

2. According to the composition of Chinese medicines of the present invention, the feet bath is adapted to use hot water to promote Chinese medicine penetrating into the foot portion throughout the whole human bodies, and further passes through all organs of the human. No appeared oral drug excess reaction will happen. The feet are fumigated over hot medicine steam about 10 minutes, and then feet bathing for 20-30 minutes. Or, simply by feet bathing the feet for 20-30 minutes will provide remarkable results. The capillaries of the feet are expanded, and the Chinese medicine passes through the capillaries to all over the human bodies.

3. In general situation, the blood pressure will reduce after 1-3 times of feet bathing, wherein dizziness, headache, and insomnia caused by the hypertension will be improved and cured, and the cure rate is high, and not recurrence.

Specific Implementations:

In order to better understand the implement of the present invention, the below implementation describes the present invention in detail. Embodiments are only cited to explain the present invention, but it is not used to limit the scope of the invention.

Case 1: accurately weight 38 grams of evodia rutaecarpa, 28 grams of chuanxiong, 25 grams of sunflower disc, 22 grams of rhizoma typhonii, 22 grams of *angelica,* 25 grams of *prunella vulgaris,* 25 grams of herba siegesbeckiae, 25 grams of *taxillus chinenesis,* 22 grams of *chamomile,* 22 grams of *astragalus,* 25 grams of *uncaria rhynchophylla,* 22 grams of *asarum,* and 22 grams of *burdock* are mixed and milled into 100-160 mesh fine powder, wherein each 40 grams of the powder form composition is sealed and packed in a bag made of spinning cloth.

Application method: (1) Add 40 grams of fine powder composition into a basin and brew and mix with 2000 ml boiling water to form a composition solution. (2) Apply steam of the composition solution for fumigating feet for 10 minutes. (3) When the composition solution cools down 40° C.-42° C., preferably adding another 2000 ml of water with a temperature of 40° C.~42° C., soak the feet of the user in the composition solution for 20-30 minutes. (4) Reply the steps (1) to (3) once per day before sleeping. The application method further comprises a step (3.1): Measure blood pressure every 20-30 minutes when the feet are soaked in the composition solution, wherein the best time to soak the feet in the composition solution is 9 p.m. and a complete course is preferable 30 days application.

Case 2: accurately weight 35 grams of evodia rutaecarpa, 25 grams of chuanxiong, 22 grams of sunflower disc, 21 grams of rhizoma typhonii, 21 grams of *angelica,* 22 grams of *prunella vulgaris,* 22 grams of herba siegesbeckiae, 22 grams of *taxillus chinenesis,* 21 grams of *chamomile,* 21 grams of *astragalus,* 22 grams of *uncaria rhynchophylla,* 21 grams of *asarum,* and 21 grams of *burdock* are mixed and milled into 100-160 mesh fine powder, wherein each 45 grams of the powder form composition is sealed and packed in a bag made of spinning cloth.

Application method: Add 45 grams of fine powder composition into a basin and brew and mix with 2000 ml boiling water to form a composition solution. (2) Apply steam of the composition solution for fumigating feet for 10 minutes. (3) When the composition solution cools down 40° C.-42° C., preferably adding another 2000 ml of water with a temperature of 40° C.~42° C., soak the feet of the user in the composition solution for 20-30 minutes. (4) Reply the steps (1) to (3) once per day before sleeping. The application method further comprises a step (3.1): Measure blood pressure every 20-30 minutes when the feet are soaked in the composition solution, wherein the best time to soak the feet in the composition solution is 9 p.m. and a complete course is preferable 30 days application.

Case 3: accurately weight 40 grams of evodia rutaecarpa, 30 grams of chuanxiong, 28 grams of sunflower disc, 24 grams of rhizoma typhonii, 24 grams of *angelica,* 28 grams of *prunella vulgaris,* 28 grams of herba siegesbeckiae, 28 grams of *taxillus chinenesis,* 24 grams of *chamomile,* 24 grams of *astragalus,* 28 grams of *uncaria rhynchophylla,* 24 grams of *asarum,* and 24 grams of *burdock* are made as decoctions, wherein the composition of Chinese medicines as mentioned above is cooked into a pot, which can be a sand pot, a ceramic pot, or a stainless steel apparatus for 1-2 hours, and each decoction can repeatedly fry two times to concentrate into 300 ml medicine liquid, wherein each 35 ml of medicine liquid is sealed and packaged into a concealed container such as a closed bag.

Application method: (1) Add 35 ml of concentrated liquid form composition of the present invention into a basin and brew and mix with 2000 ml boiling water to form a composition solution. (2) Apply steam of the composition solution for fumigating feet for 10 minutes. (3) When the composition solution cools down 40° C.-42° C., preferably adding another 2000 ml of water with a temperature of 40° C.~42° C., soak the feet of the user in the composition solution for 20-30 minutes. (4) Reply the steps (1) to (3) once per day before sleeping. The application method further comprises a step (3.1): Measure blood pressure every 20-30 minutes when the feet are soaked in the composition solution, wherein the best time to soak the feet in the composition solution is 9 p.m. and a complete course is preferable 30 days application.

Case 4: accurately weight 40 grams of evodia rutaecarpa, 30 grams of chuanxiong, 20 grams of sunflower disc, 20 grams of rhizoma typhonii, 20 grams of *angelica,* 20 grams of *prunella vulgaris,* 20 grams of herba siegesbeckiae, 20 grams of *taxillus chinenesis,* 20 grams of *chamomile,* 20 grams of *astragalus,* 20 grams of *uncaria rhynchophylla,* 20 grams of *asarum,* and 20 grams of *burdock* are made as decoctions, wherein the composition of Chinese medicines as mentioned above is cooked into a pot, which can be a sand pot, a ceramic pot, or a stainless steel apparatus for 1-2 hours, and each decoction can repeatedly fry two times to concentrate into 300 ml medicine liquid, wherein each 50 ml of medicine liquid is sealed and packaged into a concealed container such as a closed bag.

Application method: (1) Add 50 ml of concentrated liquid form composition of the present invention into a basin and brew and mix with 2000 ml boiling water to form a composition solution. (2) Apply steam of the composition solution for fumigating feet for 10 minutes. (3) When the composition solution cools down 40° C.-42° C., preferably adding another 2000 ml of water with a temperature of 40° C.~42° C., soak the feet of the user in the composition solution for 20-30 minutes. (4) Reply the steps (1) to (3) once per day before sleeping. The application method further comprises a step (3.1): Measure blood pressure every 20-30 minutes when the feet are soaked in the composition solution, wherein the best time to soak the feet in the composition solution is 9 p.m. and a complete course is preferable 30 days application.

Case 5: accurately weight 50 grams of evodia rutaecarpa, 10 grams of chuanxiong, 30 grams of sunflower disc, 25 grams of rhizoma typhonii, 25 grams of *angelica,* 30 grams of *prunella vulgaris,* 30 grams of herba siegesbeckiae, 30 grams of *taxillus chinenesis,* 25 grams of *chamomile,* 25 grams of *astragalus,* 30 grams of *uncaria rhynchophylla,* 25 grams of *asarum,* and 25 grams of *burdock* are made as decoctions, wherein the composition of Chinese medicines as mentioned above is cooked into a pot, which can be a sand pot, a ceramic pot, or a stainless steel apparatus for 1-2 hours, and each decoction can repeatedly fry two times to concentrate into 300 ml medicine liquid, wherein each 30 ml of medicine liquid is sealed and packaged into a concealed container such as a closed bag.

Application method: (1) Add 30 ml of concentrated liquid form composition of the present invention into a basin and brew and mix with 2000 ml boiling water to form a composition solution. (2) Apply steam of the composition solution for fumigating feet for 10 minutes. (3) When the composition solution cools down 40° C.-42° C., preferably adding another 2000 ml of water with a temperature of 40° C.~42° C., soak the feet of the user in the composition solution for 20-30 minutes. (4) Reply the steps (1) to (3) once per day before sleeping. The application method further comprises a step (3.1): Measure blood pressure every 20-30 minutes when the feet are soaked in the composition solution, wherein the best time to soak the feet in the composition solution is 9 p.m. and a complete course is preferable 30 days application.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An application method of a composition of Chinese medicines which includes a predetermined amount of evodia rutaecarpa, chuanxiong, sunflower disc, rhizoma typhonii, angelica, prunella vulgaris, taxillus chinensis, herba siegesbeckiae, chamomile, astragalus, uncaria rhynchophylla, asarum, and burdock, wherein the application method comprises the steps of:
    (a) adding a predetermined amount of the composition in a form selected from the group consisting of power form and decoction form into a basin for feet bathing;
    (b) brewing the composition with a predetermined amount of water having a temperature 40° C.~100° C. and well mixing to form a composition solution; and
    (c) when the composition solution being cool to 38° C.~48° C., soaking feet of a user in the composition solution for a predetermined period of time.

2. The application method, as recited in claim 1, before the step (c), further comprising a step (i) of applying steam of the composition solution with a temperature between 70° C.~80° C. for fumigating the feet of the user for about 10 minutes.

3. The application method, as recited in claim 1, further comprising a step (d) of repeating the steps (a) to (c) at least once per day at a time after dark and before dawn.

4. The application method, as recited in claim 2, further comprising a step (d) of repeating the steps (a), (b), (i), and (c) at least once per day at a time after dark and before dawn.

5. The application method, as recited in claim 3, wherein the application method is taken 30 minutes before sleeping.

6. The application method, as recited in claim 4, wherein the application method is taken 30 minutes before sleeping.

7. The application method, as recited in claim 3, wherein in the step (c), the feet is soaked in the composition solution for 20~40 minutes while the temperature of the composition solution is maintained at 40° C.~42° C.

8. The application method, as recited in claim 4, wherein in the step (c), the feet is soaked in the composition solution for 20~40 minutes while the temperature of the composition solution is maintained at 40° C.~42° C.

9. The application method, as recited in claim 1, wherein a proportion of the composition and the water is 30~50: 2000~4000.

10. The application method, as recited in claim 7, wherein a proportion of the composition and the water is 30~50: 2000~4000.

11. The application method, as recited in claim 8, wherein a proportion of the composition and the water is 30~50: 2000~4000.

12. The application method, as recited in claim 3, wherein a weight ratio of the composition is: the evodia rutaecarpa 40-50:the chuanxiong 30-40:the sunflower disc 20-30:the rhizoma typhonii 20-25:the *angelica* 20-25:the *prunella vulgaris* 20-30:the herba siegesbeckiae 20-30:the *taxillus chinensis* 20-30:the *chamomile* 20-25:the *astragalus* 20-25: the *uncaria rhynchophylla* 20-30:the *asarum* 20-25:the *burdock* 20-25.

13. The application method, as recited in claim 3, wherein a weight ratio of the composition is: the evodia rutaecarpa 35-40:the chuanxiong 25-30:the sunflower disc 22-28:the rhizoma typhonii 21-24:the *angelica* 21-24:the *prunella vulgaris* 22-28:the herba siegesbeckiae 22-28:the *taxillus chinensis* 22-28:the *chamomile* 21-24:the *astragalus* 21-24: the *uncaria rhynchophylla* 21-38:the *asarum* 21-24:the *burdock* 21-24.

14. The application method, as recited in claim 3, wherein the composition includes 38 g of the evodia rutaecarpa, 28 g of the chuanxiong, 25 g of the sunflower disc, 22 g of the rhizoma typhonii, 22 g of the *angelica,* 25 g of the *prunella vulgaris,* 25 g of the herba siegesbeckiae, 25 g of the *taxillus chinensis,* 25 g of the *chamomile,* 22 g of the *astragalus,* 25 g of the *uncaria rhynchophylla,* 22 g of the *asarum,* and 22 g of the *burdock.*

15. The application method, as recited in claim 11, wherein the composition includes 38 g of the evodia rutaecarpa, 28 g of the chuanxiong, 25 g of the sunflower disc, 22 g of the rhizoma typhonii, 22 g of the *angelica,* 25 g of the *prunella vulgaris,* 25 g of the herba siegesbeckiae, 25 g of the *taxillus chinensis,* 25 g of the *chamomile,* 22 g of the *astragalus,* 25 g of the *uncaria rhynchophylla,* 22 g of the *asarum*, and 22 g of the *burdock.*

\* \* \* \* \*